(12) United States Patent
Squires et al.

(10) Patent No.: US 6,736,821 B2
(45) Date of Patent: May 18, 2004

(54) SYSTEM AND METHOD OF MATING IMPLANTS AND VERTEBRAL BODIES

(75) Inventors: Craig M. Squires, Memphis, TN (US); Gregory C. Marik, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/174,017

(22) Filed: Jun. 18, 2002

(65) Prior Publication Data

US 2003/0233094 A1 Dec. 18, 2003

(51) Int. Cl.⁷ .............. A61F 5/00; A61F 2/30; A61B 17/00; A61B 17/14
(52) U.S. Cl. .............. 606/87; 606/69; 606/79; 606/80; 606/181
(58) Field of Search .............. 606/69, 79, 80, 606/81, 82, 87, 88, 181

(56) References Cited

U.S. PATENT DOCUMENTS

| | | | | |
|---|---|---|---|---|
| 651,921 A | * | 6/1900 | De Vilbiss | .............. 606/172 |
| 4,059,115 A | * | 11/1977 | Jumashev et al. | ............ 606/82 |
| 6,083,228 A | | 7/2000 | Michelson | |
| 6,120,506 A | * | 9/2000 | Kohrs et al. | .................. 606/80 |
| 6,159,214 A | | 12/2000 | Michelson | |
| 6,226,548 B1 | | 5/2001 | Foley et al. | |
| 6,236,875 B1 | | 5/2001 | Bucholz et al. | |
| 6,348,058 B1 | | 2/2002 | Melkent et al. | |
| 2001/0034526 A1 | * | 10/2001 | Kuslich et al. | ............... 606/80 |

* cited by examiner

Primary Examiner—Pedro Philogene
(74) Attorney, Agent, or Firm—Coats & Bennett, PLLC (57) ABSTRACT

A system and method of contouring a perimeter surface of a vertebral body. The invention includes positioning a reference mechanism relative to one or more vertebral bodies. In one embodiment, the reference mechanism is positioned relative to the disc space between adjacent vertebral bodies. The reference mechanism may have a variety of forms, including mechanical, computerized, and visual. A bone removal mechanism is aligned with the reference mechanism to contour the vertebral body or bodies. A predetermined relationship exists between the bone removal mechanism and the reference mechanism. The predetermined relationship provides for the bone removal mechanism to contour the vertebral body or bodies in a precise fashion.

14 Claims, 6 Drawing Sheets

SYSTEM AND METHOD OF MATING IMPLANTS AND VERTEBRAL BODIES

BACKGROUND OF THE INVENTION

Devices are often mounted on the perimeter surface of vertebral bodies during surgery. Examples include attaching a plate or ligament to connect adjacent vertebral bodies. It is important that the device be properly positioned along the vertebrae, and that the device be firmly attached to the vertebral body. These two aspects will result in the device operating properly, and to cause more consistent and expected results. Poor placement or attachment may cause the device to not operate properly, or move relative to the vertebral body. These occurrences result in either pain to the patient, or may result in the device failing or breaking free from the vertebral body.

Proper alignment and attachment of the devices is often difficult because of variations in the shape and contours of the vertebral body. Poor surface contact between the device and the vertebral body results if the device is mounted over variations in the surface of the vertebral body. It is not necessary that the entire device surface contact the vertebral body, but better results are obtained by greater contact. Poor surface contact may result in the over-stressing the fasteners or device that attach to the vertebral body. This in turn may result in the fasteners pulling loose from the vertebral body, or the device or the fasteners failing. Either of these results is detrimental to the patient.

It may be more difficult for the surgeon to mount the device if there is not an adequate mounting surface on the vertebral body. The surgeon may be forced to mount the device in an area other than the preferred location on the vertebral body. This may result in the device not operating to the fullest capacity. The non-preferred placement may also be a more difficult procedure for the surgeon which may require a higher degree of skill, or possibly take a longer time to complete.

SUMMARY OF THE INVENTION

The present invention is directed to a system and method of contouring a perimeter surface of a vertebral body. The invention comprises positioning a reference mechanism relative to one or more vertebral bodies. In one embodiment, the reference mechanism is positioned relative to the disc space between adjacent vertebral bodies. The reference mechanism may have a variety of forms, including mechanical, computerized, and visual. A bone removal mechanism is aligned with the reference mechanism to contour the vertebral body or bodies. A predetermined relationship exists between the bone removal mechanism and the reference mechanism. The predetermined relationship provides for the bone removal mechanism to contour the vertebral body or bodies in a precise fashion.

In one embodiment, the device includes a trial and a bone surface preparation device. The trial may include a spacer having first and second contact surfaces that are spaced a distance apart to contact end plates of adjacent vertebral bodies. A guide may extend outward from the spacer at a variety of angles depending upon the specific application for the device. The bone surface preparation device may be a cannulated member having an opening that extends over the guide. The device may include a cutting head having a blade that extends the entire section around the opening, or at least around a portion of the section.

In use, one method includes inserting the trial into the patient with the spacer positioned between adjacent vertebral bodies and the guide extending outward. The bone surface preparation device may be inserted over the guide and slid down to a point where the blade contacts the perimeter surface of at least one of the vertebral bodies. The device may then be powered such that the blade rotates and the blade shapes and contours the perimeter surface of one or both of the vertebral bodies.

DETAILED DESCRIPTION

The present invention is directed to a system and method of contouring a perimeter surface of a vertebral body. As illustrated schematically in FIG. 1, a reference mechanism 19 is positioned relative to one or more vertebral bodies 120. The reference mechanism 19 may align with one or two of the vertebral bodies 120, or may align with the spacing between the vertebral bodies. A bone surface preparation mechanism 18 is then positioned relative to the reference mechanism 19 to contact one or more of the vertebral bodies 120. The bone surface preparation mechanism 18 contours the surface of one or more vertebral bodies 120. With alignment being performed in this manner, the bone surface preparation mechanism 18 is established at a predetermined position relative to the one or more vertebral bodies 120. The term vertebral body is used generally to describe the vertebral geometry comprising the vertebral member, pedicles, lamina, and processes.

Figure 1:
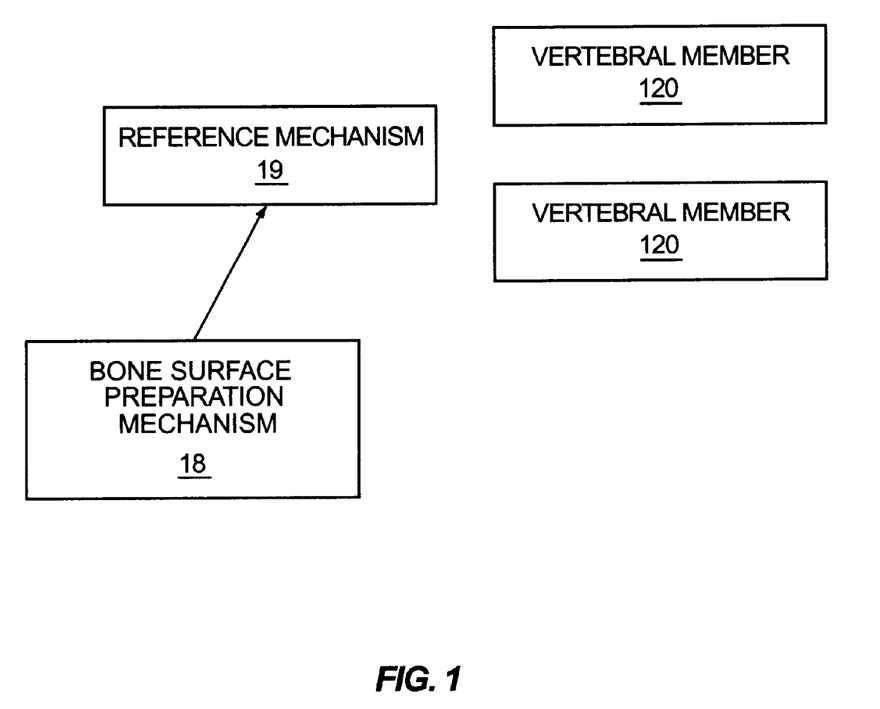
FIG. 1 is a schematic representation of the present invention in accordance with one embodiment.

The reference mechanism 19 may be a mechanical device, computerized, or a visual alignment tool. The reference mechanism 19 provides a medium for guiding the mechanism 18 to contact the vertebral bodies 120. Examples of reference mechanisms are disclosed in U.S. Pat. Nos. 6,348,058, 6,236,875, and 6,226,548, each incorporated herein in their entirety.

The bone surface preparation mechanism 18 contours the external surface of the vertebral bodies 120. Various embodiments of contouring mechanisms may be useful in the present invention including, but not limited to, burrs, router bits, abraders, grinders, rasps, drills, graters, saws, oscillating cutters, vibrating cutters, reciprocating cutters, orbital cutters, rotating cutters, and lasers.

Figure 2:
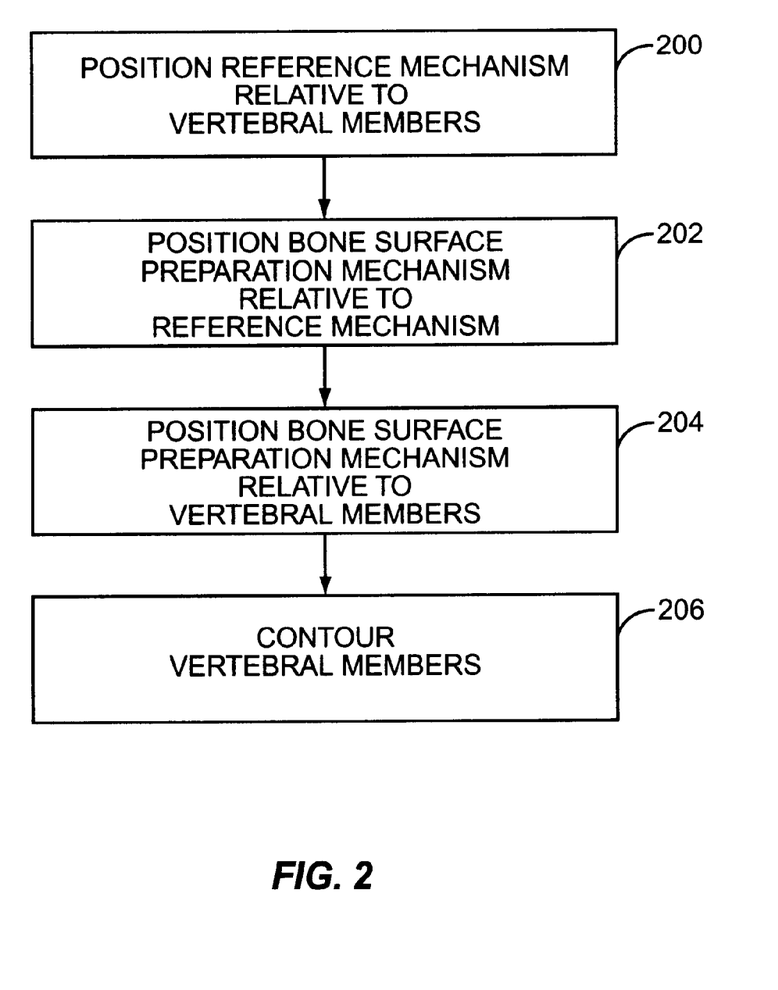
FIG. 2 is a flowchart illustrating the steps of using the present invention in accordance with one embodiment.

FIG. 2 illustrates a flowchart of the steps of using the present invention for contouring one or more vertebral bodies 120. Initially, the reference mechanism 19 is positioned relative to one or more vertebral bodies 120 (step 200). The reference mechanism 19 may be aligned mechanically, by a computerized method, or by visual or imaging alignment. The reference mechanism 19 may be aligned by the spacing between the vertebral bodies 120, the vertebral bodies themselves, or by other alignment. The bone surface preparation mechanism 18 is positioned relative to the reference mechanism 19 (step 202). Positioning may be by mechanically attaching the two mechanisms 18, 19, a computer alignment aspect of the two mechanisms, or other like method. Because the reference mechanism 19 is aligned relative to one or more of the vertebral bodies 120, the bone surface preparation mechanism is also aligned relative to the one or more of the vertebral bodies 120 (step 204). The alignment of the bone surface preparation mechanism 18 is caused by the predetermined relationship between the reference mechanism 19 and bone surface preparation mechanism 18. Once aligned by the predetermined relationship, the bone surface preparation mechanism 18 can contour the external surface of the vertebral bodies 120. The method can be used for contouring a single vertebral body 120, or more than one vertebral body.

Figure 3:
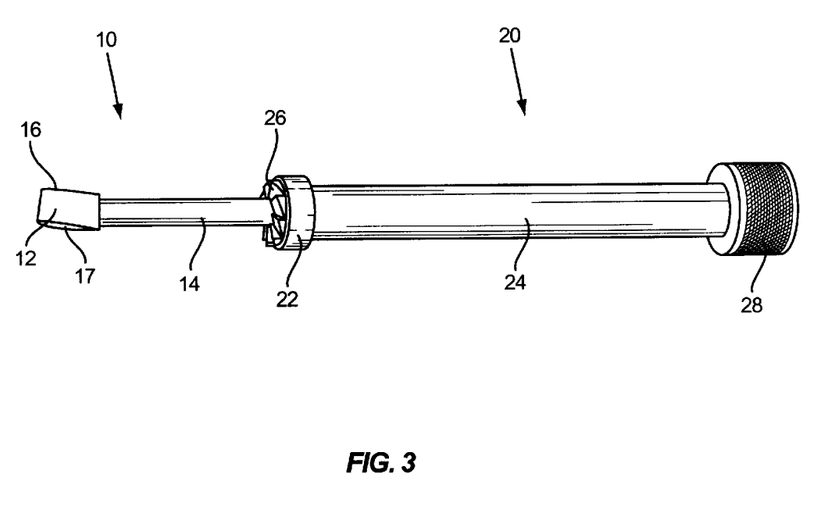
FIG. 3 is perspective view of a trial inserted within a bone shaping device according to one embodiment of the present invention.

One embodiment of the invention is illustrated in FIG. 3 and includes a trial 10 having a spacer 12 and a guide 14. The spacer 12 is sized to be positioned between two vertebral bodies and the guide 14 is attached to and extends outward from the spacer 12. A contouring device 20 is inserted along the guide 14 to access a perimeter surface of at least one of the vertebral bodies 120. The device 20 includes a cutting head 22 for shaping and contouring at least one of the bodies, and a receiver 24 for receiving the guide 14 for placing the cutting head 22 relative to at least one of the vertebral bodies 120.

The spacer 12 includes a first surface 16 and a second surface 17 each sized to contact the end plates of the adjacent vertebral bodies. In one embodiment, the first surface 16 is substantially parallel to the second surface 17. The spacer 12 may have a variety of widths to fit between different vertebral bodies along the spine. By way of example, a spacer 12 for use in the upper cervical region of the spine may have a narrower width than a spacer for use in the lower cervical region. In one embodiment, the widths of spacers 12 for use in the cervical region range from about 6 millimeters to about 10 millimeters. The elongated guide 14 is connected to and extends outward from the width of the spacer 12. In one embodiment, guide 14 is connected to a midpoint of the spacer 12 an equal distance between the first and second surfaces 16, 17. In another embodiment, guide 14 connects to the width of the spacer 12 at a point closer to one of the first or second surfaces 16, 17.

The guide 14 is connected to and extends outward from the spacer 12. In one embodiment, the guide has a length such that an end opposite the spacer 12 extends outside of a patient's body when the spacer is positioned between the vertebral bodies. The guide 14 is substantially linear and may extend outward from the spacer 12 at a variety of angles. The angle may vary depending upon the position along the spine and the amount of lordosis. In one embodiment, the guide 14 has a circular cross-sectional shape.

The contouring device 20 includes a cutting head 22 and a receiver 24. The cutting head 22 and receiver 24 may be fixedly attached, or the cutting head 22 may be rotatably mounted to the receiver 24. In either event, blades 26 mounted to the distal end of the cutting head 22 contact the perimeter surface of the vertebral body to contour and shape the body. Blades 26 may have a variety of configurations as is well known in the art. In one embodiment, the blades 26 are mounted at an end of the device 20 and are substantially perpendicular to the axis of the device 20. In another embodiment, the blades 26 are mounted at an angle relative to the axis of the device 20. The blades 26 may extend continuously about the entire periphery of the cutting head 22, or the blades 26 may be positioned at a discrete segment or segments along the periphery.

In one embodiment, the device 20 is a cannula having a hollow interior that extends the entire length to mount over the guide 14. In one embodiment, the cross-sectional shape and size of the opening is consistent through the length. In another embodiment, the cross-sectional shape and size of the opening is different within the cutting head 22 than through the receiver 24. In one embodiment, the opening extending through the device 20 is substantially circular to match the shape of the guide 14 such that it may be rotated about the guide 14. A mount 28 may be positioned at the end of the device 20 opposite the cutting head 22. Mount 28 connects the device 20 to a power source for rotating the cutting head 22, or rotating the cutting head 22 and receiver 24 depending upon the embodiment. Mount 28 may include threads for connecting to the power source, or may include other well-known connection means.

A variety of different power sources may drive the blade 26. Embodiments include a rechargeable battery, gas turbine mechanism, and any standard electrical source, such as 110 volt, 60 cycle power sources, with or without a transformer to reduce the voltage as necessary.

In one embodiment, the trial 10 and device 20 are separate members that are mated together during the shaping and contouring procedure. In another embodiment, the trial 10 is slidably connected to the device 20 such that the two members cannot be separated.

Figure 4:
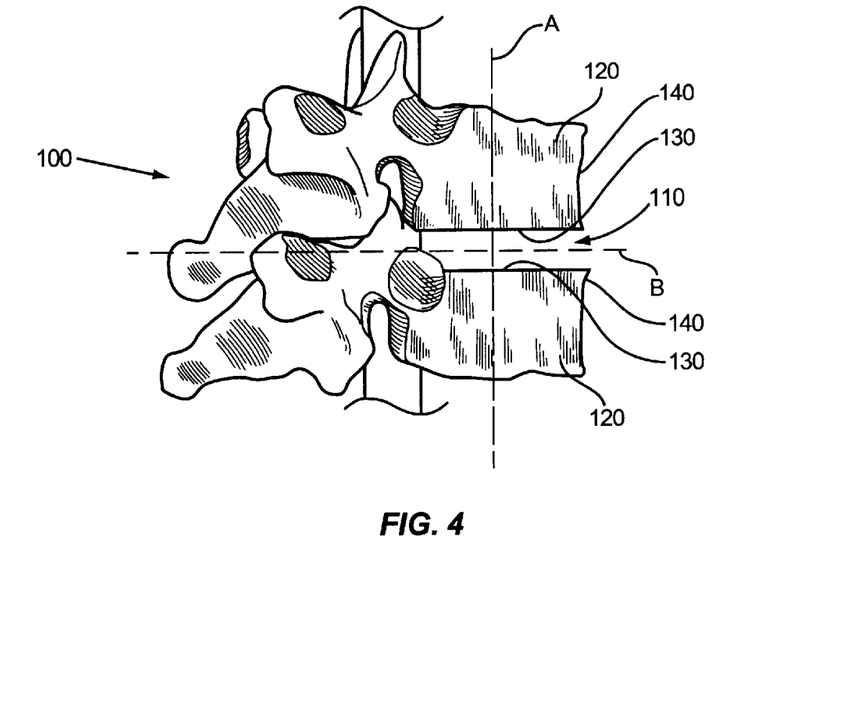
FIG. 4 is a side view of a vertebral segment illustrating the adjacent vertebral bodies and the disc space therebetween.

FIG. 4 illustrates a side view of a vertebral segment 100 including a pair of vertebral bodies 120. Each vertebral body 120 includes a perimeter surface 140 with the superior and inferior ends having an end plate 130. Adjacent vertebral bodies 120 are positioned a distance apart with a disc space 110 formed therebetween. In one embodiment, the intervertebral disc has been removed to provide for an insert, such as a fusion device or articulating member, to be placed between the vertebral bodies 120. In one embodiment, each of the end plates 130 has been prepared for receiving the insert. Each end plate 130 includes a cartilaginous external layer and a bony internal layer. The preparation may include removing the external layer while leaving as much of the bony internal layer as possible. In one embodiment, the preparation includes performing a Smith-Robinson procedure to form two opposing substantially parallel surfaces. In another embodiment, the end plates 130 are prepared using a Cloward procedure. In another embodiment, the end plates 130 are prepared with curved surfaces.

A midline A extends through the vertebral segment 100 through each vertebral body 120 and disc space 110. This midline is referred to as a vertebral segment midline. A second midline B extends through the disc space 110 formed between adjacent vertebral bodies 120. This midline is referred to as a disc midline.

Figure 5:
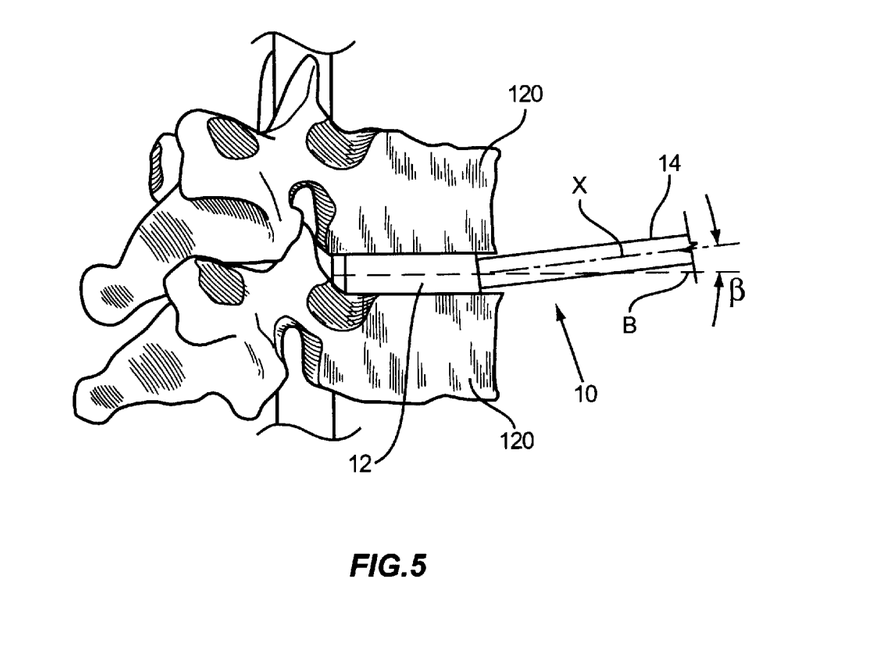
FIG. 5 is side view illustrating the trial inserted within the vertebral segment with the spacer contacting end plates of the adjacent vertebral bodies and the guide extending outward therefrom according to one embodiment of the present invention.

FIG. 5 illustrates the spacer 12 positioned within the disc space 110 between two adjacent vertebral bodies 120. The spacer first surface 16 is contacting an end plate of a first vertebral body and the spacer second surface 17 is contacting an end plate of a second vertebral body. The guide 14 extends outward from the spacer 12. An axis of the guide, illustrated as X, intersects the disc midline B at an angle β. In one embodiment, the guide axis X is parallel with the disc midline B (i.e., β is zero degrees). In other embodiments, the angle β ranges between about +/−20 degrees relative to parallel.

Figure 6:
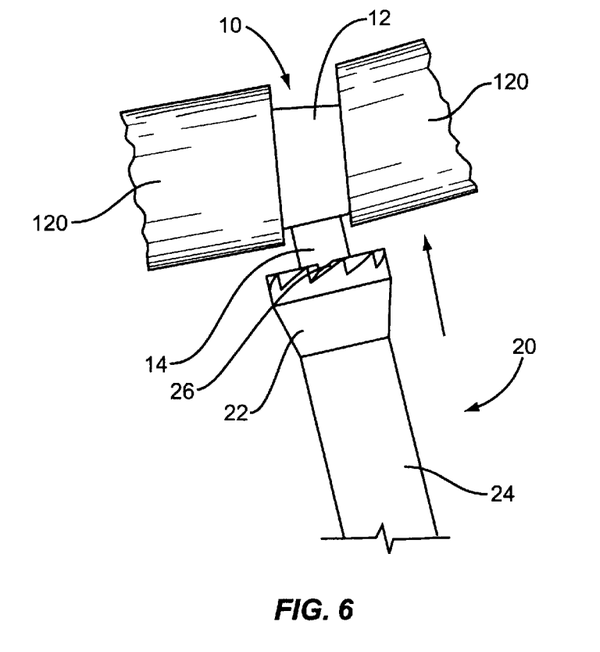
FIG. 6 is a partial side view of the bone surface preparation device being inserted along the guide towards the vertebral bodies according to one embodiment of the present invention.
Figure 7:
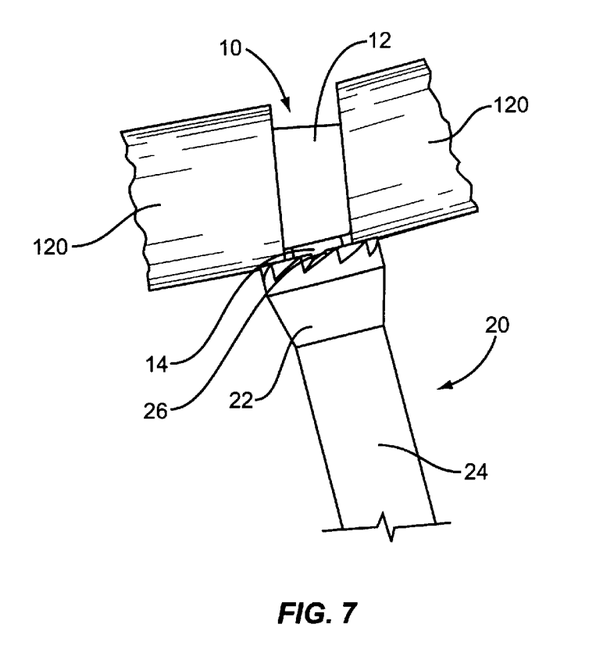
FIG. 7 is a partial side view of the bone surface preparation device contacting the perimeter surfaces of the vertebral bodies according to one embodiment of the present invention.

Once the trial 10 is positioned, the bone surface preparation device 20 is inserted along the guide 14 to access one or more of the vertebral bodies 120 as illustrated in FIGS. 6 and 7. In the embodiment illustrated in FIGS. 6 and 7, the device 20 is cannulated and is inserted over the guide 14. The blades 26 at the distal end of the device 20 contact the perimeter surface of one or more of the vertebral bodies 120. The cutting head 22 is rotated such that the blades 26 shape and contour the perimeter surfaces. The embodiment illustrated shows both adjacent vertebral bodies 120 being shaped and contoured. In another embodiment, the blades 26 only contact one vertebral body 120.

Figure 8:
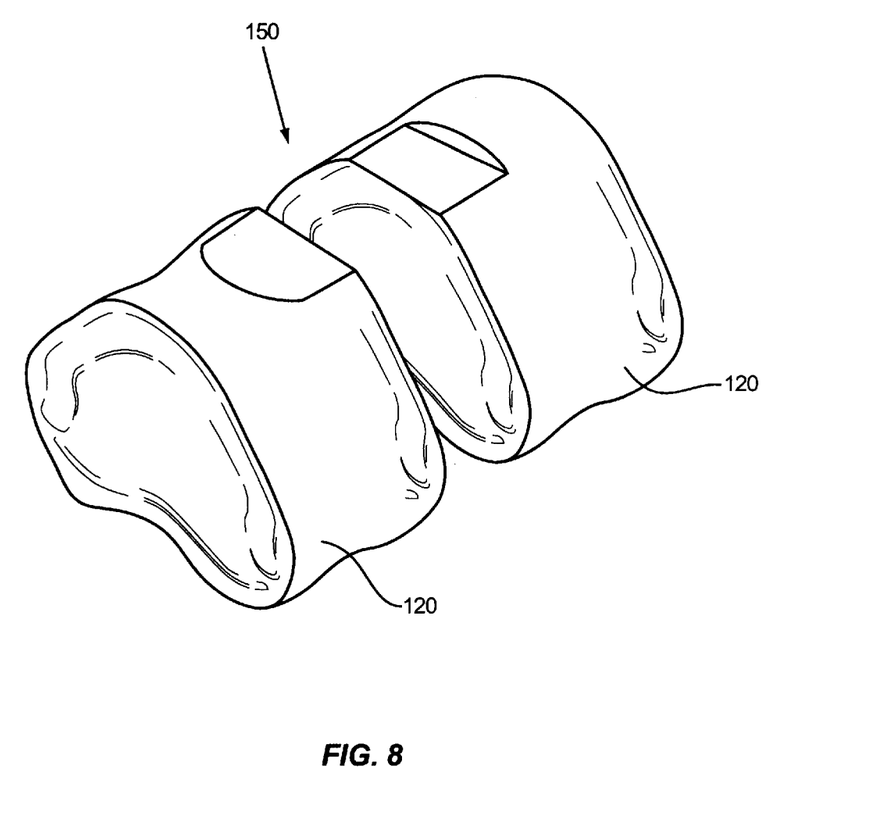
FIG. 8 is perspective view illustrating the contours removed from the vertebral bodies according to one embodiment of the present invention.

The contour may include a substantially flat surface, cone shaped surface, or curved surface. FIG. 8 illustrates one embodiment of contouring the perimeter surface of both vertebral bodies 120. This provides for a mounting surface for installing a plate, ligament, or other like device that span between and connect the vertebral bodies 120. In one embodiment, about 2 millimeters is contoured from the vertebral body 120. In another embodiment (not illustrated), only one of the perimeter surfaces of the vertebral bodies 120 is contoured. The contours 150 may have a variety of shapes depending upon the configuration of the blades 26. Additionally, both adjacent vertebral bodies 120 may have the same contour 150, or each may be contoured to have different sizes and shapes of contours. The contouring procedure may remove any amount of the perimeter surface of the vertebral body 120.

In use, the disc space 110 is prepared for receiving the trial 10. The trial 10 is inserted within the patient with the spacer first surface 16 contacting the end plate 130 of the first vertebral body 120, and the spacer second surface 17 contacting the end plate 130 of the second vertebral body 120. In one embodiment, a number of spacers of different widths are inserted until the surgeon determines the sized spacer 12 with a width that fits best within the disc space 110. In one embodiment, the best fit is the spacer 12 that contacts the end plates 130 without expanding the size of the disc space 110. The guide 14 extends outward from the vertebral bodies 120 when the spacer 12 is inserted.

The bone surface preparation device 20 is inserted over the guide 14. The opening that extends through the device 20 is inserted over the guide 14 such that the device can be slid relative to the guide 14. The device 20 is slid along the guide 14 a distance for the blade 26 located on the distal end to contact the perimeter surface of one or both vertebral bodies adjacent to the spacer 12. The device 20 is activated such that the cutting head 22 with blade 26 rotates to contour the perimeter surface. Because the blade 26 is aligned relative to the trial 10, the perimeter surface will be prepared at a prescribed geometry and orientation relative to the disc space 110. The perimeter surface is prepared to match the contour of a surface of the insert to be implanted. Once the perimeter surface is adequately contoured, the device 20 is removed from the guide, and the trial is removed from between the adjacent vertebral bodies 120.

In one embodiment, the present invention is used for contouring and shaping vertebral bodies within the cervical region of the spine. In other embodiments, the present invention is used for shaping and contouring vertebral bodies within the thoracic and lumbar regions of the spine. In one embodiment, the present invention is used for shaping and contouring the anterior section of a vertebral body. In another embodiment, the invention is used for shaping and contouring a posterior section of a vertebral body. In another embodiment, the invention is used for contouring a lateral section of a vertebral body.

In another embodiment, the bone surface preparation device 20 attaches to the guide 14, i.e., the device is not slid over the guide 14. The device 20 is slid along the guide 14 such that the blades 26 contact the perimeter surface of one or more vertebral bodies.

The present invention may be carried out in other specific ways than those herein set forth without departing from the scope and essential characteristics of the invention. The trial 10 and bone surface preparation device 20 may be constructed of a variety of materials including stainless steel. The present embodiments are, therefore, to be considered in all respects as illustrative and not restrictive, and all changes coming within the meaning and equivalency range of the appended claims are intended to be embraced therein.

What is claimed is:

1. A method of contouring a perimeter surface of a vertebral body comprising the steps of:

aligning a reference mechanism with a vertebral body by positioning a spacer within a disc space to support the vertebral body and a second vertebral body with a guide extending outward from the spacer at an angular relationship relative to a mid-line of the disc space;

guiding a bone surface preparation mechanism along the reference mechanism to contact the vertebral body, the bone surface preparation mechanism being aligned with the vertebral body at a predetermined relationship; and contouring a perimeter surface of the vertebral body with the bone surface preparation mechanism, the perimeter surface being contoured relative to the predetermined relationship.

2. A method of contouring a perimeter surface of a vertebral body comprising the steps of:

inserting a trial within a disc space formed between vertebral bodies, the trial comprising a spacer and a guide with the spacer being positioned between the vertebral bodies and having first and second substantially parallel surfaces that contact and support the vertebral bodies and Position the guide to extend outward from the spacer at an angle of between about 0 to 20 degrees relative to a disc midline;

inserting a cannulated bone surface preparation device over the guide and contacting a blade on a distal end of the bone surface preparation device against a perimeter surface of one of the vertebral bodies; and shaping a perimeter surface of at least one of the vertebral bodies.

3. The method of claim 2, wherein the spacer has a width to fit between adjacent vertebral bodies in a cervical portion of the spine.

4. The method of claim 2, wherein the guide is connected to the spacer at a point centered between the first and second substantially parallel surfaces.

5. The method of claim 2, wherein the step of shaping the perimeter surface of at least one of the vertebral bodies comprises forming the perimeter surface to be flat and substantially perpendicular to an axis of the guide.

6. The method of claim 2, wherein the step of shaping the perimeter surface of the vertebral body comprises shaping the perimeter surface in an area adjacent to an end plate.

7. The method of claim 2, wherein the step of shaping the perimeter surface of at least one of the vertebral bodies comprises rotating the blade about the guide and contacting the blade against the perimeter surface.

8. The method of claim 2, further comprising contouring the second vertebral body.

9. A method of preparing a perimeter surface of a vertebral body, comprising the steps of:

inserting a spacer between adjacent vertebral bodies with a spacer first surface contacting an end plate of a first vertebral body and a second surface contacting an end plate of a second vertebral body to position a guide that extends outward from the spacer at an angle relative to the vertebral bodies;

engaging a bone surface preparation device to the guide;

positioning the bone surface preparation device against a perimeter surface of the first vertebral body; and removing a portion of the perimeter surface of the first vertebral body with the bone surface preparation device, the portion being within a predetermined distance of the guide.

10. The method of claim 9, wherein the step of removing the portion of the perimeter surface of the first vertebral body with the bone surface preparation device comprises forming a flat surface on the perimeter surface of the vertebral body.

11. A method of preparing perimeter surfaces of adjacent vertebral bodies comprising the steps of:

preparing a disc space between adjacent vertebral bodies such that end plates of a first vertebral body and end plates of a second vertebral body are substantially parallel;

inserting a spacer within the disc space, the spacer having a body with two substantially parallel sides with a first side contacting the end plate of the first vertebral body and a second side contacting the end plate of the second vertebral body, the spacer further comprising an elongated guide that extends outward from the body at an angle relative to the disc space and determined by the positioning of the spacer within the disc space;

positioning a bone surface preparation device against a perimeter surface of the first vertebral body and a perimeter surface of the second vertebral body; and contouring an area of the perimeter surface of the first perimeter body and the second vertebral body, the area being within a given distance of the guide and having a prescribed geometry and a prescribed orientation relative to the disc space.

12. A method of contouring vertebral bodies comprising the steps of:

positioning a guide relative to a vertebral body with a first end adjacent to the vertebral body and a second end spaced away from the vertebral body, the guide being positioned at an angle relative to a mid-plane of the vertebral body;

inserting a receiving portion of a bone surface preparation device over the second end of the guide and sliding the device along the guide such that a distal end contacts a perimeter surface of the vertebral body, the distal end having a flat cutting surface aligned substantially perpendicular to an axis of the guide; and activating the bone surface preparation device and removing a portion of the perimeter surface of the vertebral body, the portion having a prescribed geometry and orientation relative to the mid-plane of the vertebral body.

13. A method of contouring a vertebral body comprising the steps of:

inserting a spacer within a disc space between a first vertebral body and a second vertebral body;

contacting a first side of the spacer with the first vertebral body and contacting a second side of the spacer with the second vertebral body;

supporting the first vertebral body and the second vertebral body with the spacer;

guiding a bone surface preparation mechanism along a guide that extends from the spacer at an angle relative to the disc space; and while the spacer is contacting the first vertebral body and the second vertebral body and aligning the guide, contouring a perimeter surface of the first vertebral body.

14. The method of claim 13, further comprising contouring the second vertebral body.

* * * * *